United States Patent [19]
VanWagenen et al.

[11] Patent Number: 5,648,540
[45] Date of Patent: Jul. 15, 1997

[54] AMINE PREPARATION

[75] Inventors: Bradford C. VanWagenen, Salt Lake City, Utah; Steven R. Duff, De Soto; William A. Nelson, Lawrence, both of Kans.; Thomas E. D'Ambra, North Greenbush, N.Y.

[73] Assignee: NPS Pharmaceuticals, Inc., Salt Lake City, Utah

[21] Appl. No.: 446,491

[22] Filed: May 22, 1995

Related U.S. Application Data

[62] Division of Ser. No. 276,214, Jul. 15, 1994, Pat. No. 5,504,253.

[51] Int. Cl.$^6$ ............ C07C 209/50; C07C 209/52
[52] U.S. Cl. .............................. 564/375; 564/374
[58] Field of Search .................. 564/374, 375

[56] References Cited

U.S. PATENT DOCUMENTS

| | | | |
|---|---|---|---|
| 2,798,094 | 7/1957 | Shepard et al. | 564/374 |
| 4,024,274 | 5/1977 | Druckrey et al. | 514/466 |
| 4,925,664 | 5/1990 | Jackson et al. | 424/537 |
| 5,064,657 | 11/1991 | Jackson et al. | 424/537 |
| 5,300,437 | 4/1994 | Stirling et al. | 435/280 |
| 5,326,784 | 7/1994 | Junien et al. | 514/456 |

FOREIGN PATENT DOCUMENTS

| | | |
|---|---|---|
| 5841847 | 3/1983 | Japan. |
| WO93/04373 | 3/1993 | WIPO. |

OTHER PUBLICATIONS

Marino et al., "An Improved Synthesis of 3-Methyl-5-Hydroxy Protected Indoles", Synthetic Communications, 24(6), pp. 839-848, Mar. 1994.

J. Brussee et al., "Synthesis of Optically Active Ethanolamines", Tetrahedron, vol. 46, No. 5, pp. 1653-1658, 1990.

P. Zandbergen et al., "A One-Pot Reduction-Transimination-Reduction Synthesis of N-substituted β-Ethanolamines from Cyanohydrins.", Tetrahedron, vol. 48, No. 19, pp. 3977-3982, 1992.

"ASN Program & Abstracts", Journ. Am. Soc. Neph., vol. 4, No. 3, 120P, 69P, pp.719, Sep., 1993.

Barnes et al., "The Use of 4-Substituted Hydrindenes in the Preparation of Cyclopentanophenanthrene Derivatives", Journ. Am. Chem. Soc., vol. 71, pp. 2644-2647, Aug. 1949.

Barney et al., "A Convenient Synthesis Of Hindered Amines And α-Trifluoromethylamines From Ketones", Tetrahedron Letters, vol. 31, No. 39, pp. 5547-5550, 1990.

Chemical Abstracts, 99:104949b, 1983, vol. 99, p. 558.

Chemical Abstracts, 116:128255t, 1992, vol. 116, p. 823.

1993 Program & Abstracts, Journal of Bone and Mineral Research, vol. 8, Supplement 1, pp. S175, S181, Aug., 1993.

Jasys et al., "The Total Synthesis of Argiotoxins 636, 659 And 673", Tetrahedron Letters, vol. 29, No. 48, pp. 6223-6226, 1988.

Mattson et al., "An Improved Method for Reductive Alkylation of Amines Using Titanium (IV) Isopropoxide and Sodium Cyanoborohydride", J. Org. Chem., vol. 55, No. 8, pp. 2552-2554, 1990.

Nason et al., "Synthesis of Neurotoxic Nephila Spider Venoms: NSTX-3 and JSTX-3", Tetrahedron Letters, vol. 30, No. 18, pp. 2337-2340, 1989.

Sheldon, Roger A., "The Industrial Synthesis Of Pure Enantiomers", Drug Information Journal, vol. 24, pp. 129-139, 1990.

*Primary Examiner*—Richard L. Raymond
*Attorney, Agent, or Firm*—Trask, Britt & Rossa

[57] ABSTRACT

A method of making (R)-N-[1-(3-methoxyphenyl)ethyl]-3-(2-chlorobenzene)propanamine which involves reducing the appropriate amidyl or iminyl precursor with an appropriate reducing agent. The appropriate amidyl or iminyl precursor is made from a synthesis involving the use of (R)-3-methoxy-α-methylbenzylamine. A method of condensing a nitrile with a primary or secondary amine to form an imine involves the reaction of a nitrile with diisobutylaluminum hydride; and then reacting the resultant compound with a primary or secondary amine to form the imine. The process is especially useful for producing enantiomerically pure chiral imines, and, ultimately, amines. Typical such imines have the formula:

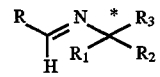

wherein R, $R_1$, $R_2$ and $R_3$ are independently selected from the group consisting of hydrogen, substituted or unsubstituted alkyl, aryl and aralkyl.

5 Claims, 6 Drawing Sheets

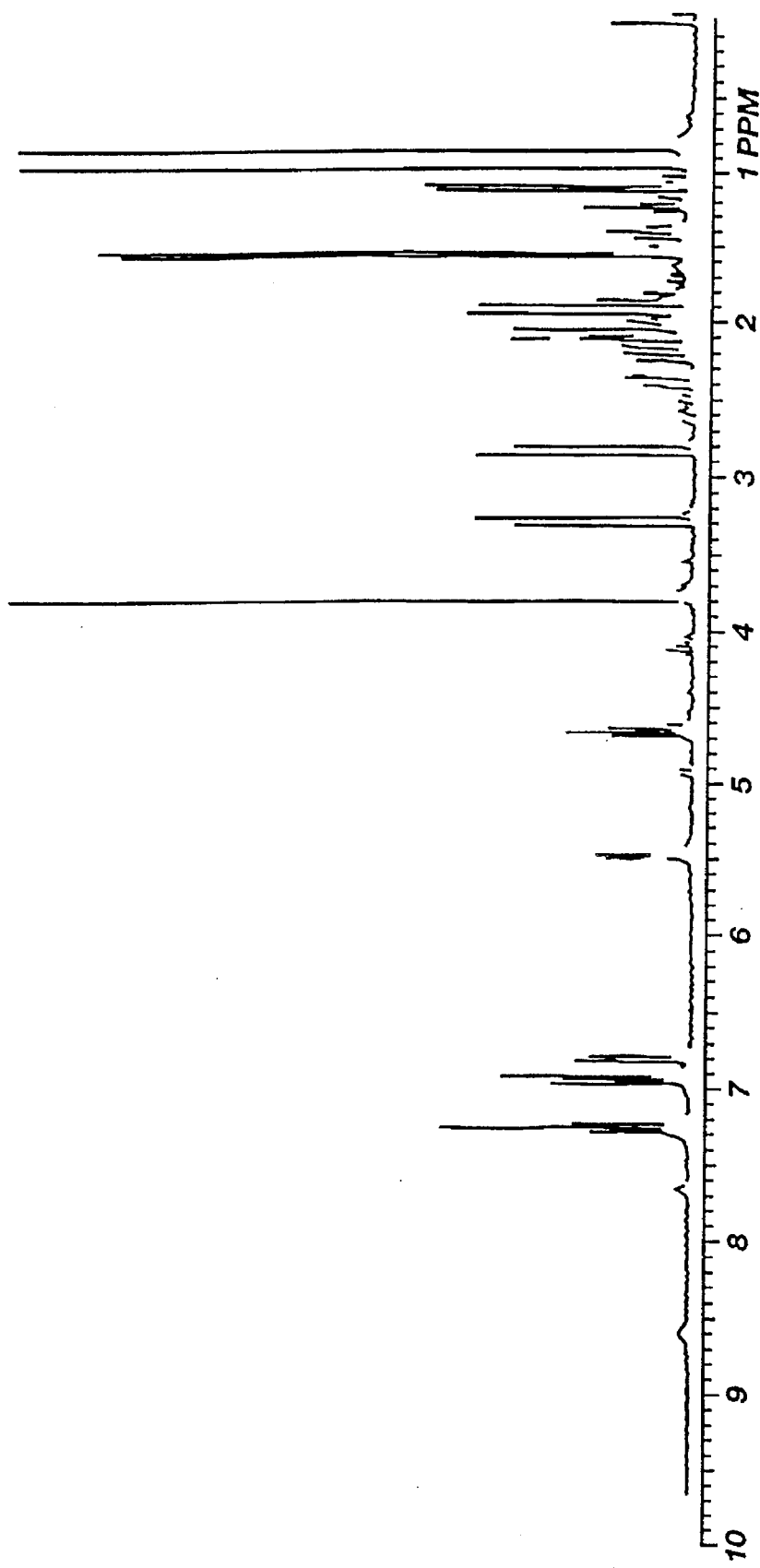

AMINE PREPARATION

This a division of application Ser. No. 08/276,214, filed Jul. 15, 1994, now U.S. Pat. No. 5,504,253.

TECHNICAL FIELD

The invention relates to a method for preparing achiral or chiral imines and/or achiral or chiral amines.

BACKGROUND

As disclosed in Fox et al. "A First Generation Calcimimetic compound (NPS R-568) that acts on the Parathyroid Cell Calcium Receptor: A Novel Therapeutic Approach for Hyperparathyroidism," *Journal of Bone and Mineral Research*, 8:S181, abstract 260 (Suppl. 1, Aug. 1993), compounds such as (R)-N-[1-(3-methoxyphenyl)ethyl]-3-(2-chlorobenzene) propanamine (also known as N-[3-(2-chlorophenyl)propyl]-R-α-methyl-3-methoxybenzylamine, (R)-N-(3-methoxyphenylethyl)-3-(2'-chlorophenyl)-1-propanamine or "NPS R-568"), i.e.:

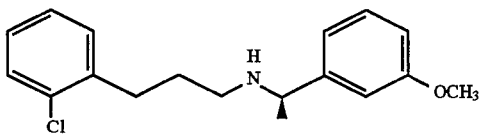

have utility in the treatment of hyperparathyroidism and possibly other bone and mineral related disorders and diseases.

A straight-forward chemical synthesis for such compounds would be an improvement in the art.

DISCLOSURE OF THE INVENTION

The invention includes a method of making (R)-N-[1-(3-methoxyphenyl)ethyl]-3-(2-chlorobenzene) propanamine which involves reducing the appropriate amide or imine precursor, i.e.:

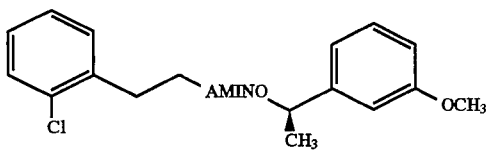

wherein amino is either

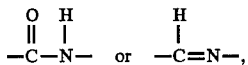

with an appropriate reducing agent. The appropriate amide or imine precursor will generally be made from a synthesis involving the use of (R)-3-methoxy-α-methylbenzylamine.

The invention further relates to a general process for condensing a nitrile with a primary or secondary amine to form an imine. The method involves reacting a nitrile with diisobutylaluminum hydride (DIBAL-H), and then reacting the resultant complex with a chosen primary or secondary amine to form an intermediate imine.

The DIBAL-H embodiment of the inventive process is especially useful for producing enantiomerically pure chiral imines, and, ultimately, amines. Typically such imines have the formula:

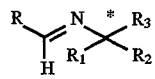

wherein R, R$_1$, R$_2$ and R$_3$ are independently selected from the group consisting of hydrogen, substituted or unsubstituted alkyl, aryl and aralkyl.

After synthesis of the imine, it will typically be reduced to an amine of the formula:

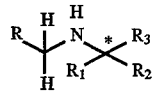

wherein R, R$_1$, R$_2$ and R$_3$ are as previously defined.

The DIBAL-H mediated condensation of amines with nitriles has broad application, affords good yields, and does not require the use of excess amine or nitrile.

BRIEF DESCRIPTION OF THE DRAWINGS

FIG. 6 is a plot of a 200 MHz $^1$H NMR (CDCl$_3$) of camphorsulfonamide obtained from reaction of 3-methoxybenzylamine with (+)-camphorsulfonyl chloride. The 3-methoxy-α-methylbenzylamine was previously isolated as the free base after two recrystallizations with (R)-(−)-mandelic acid.

BEST MODE OF THE INVENTION

Figure 1:
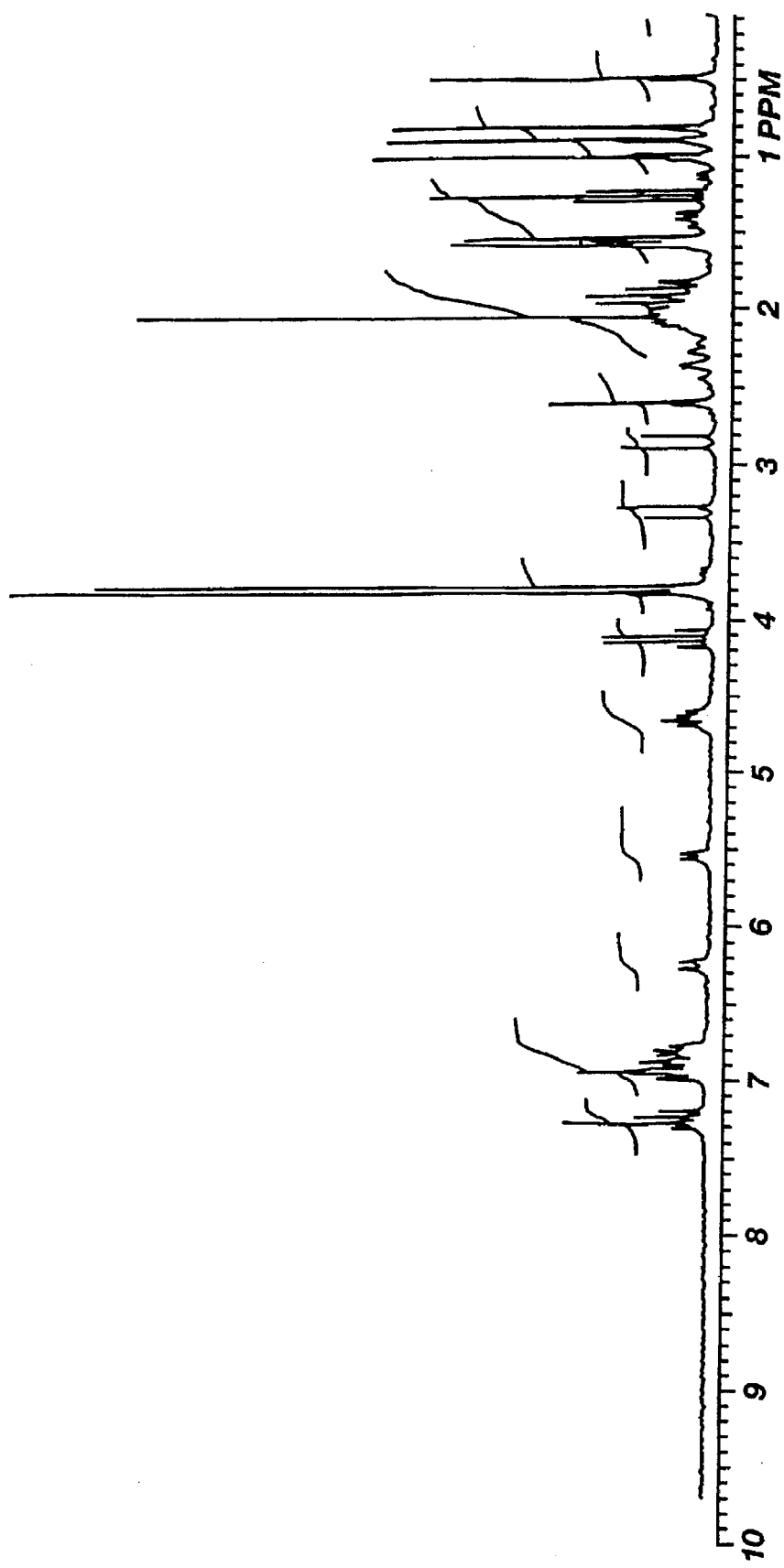
FIG. 1 is a plot of a 200 MHz $^1$H NMR (CDCl$_3$) of camphorsulfonamides obtained from reaction of racemic 3-methoxy-α-methylbenzylamine with (+)-10-camphorsulfonyl chloride.
Figure 2:
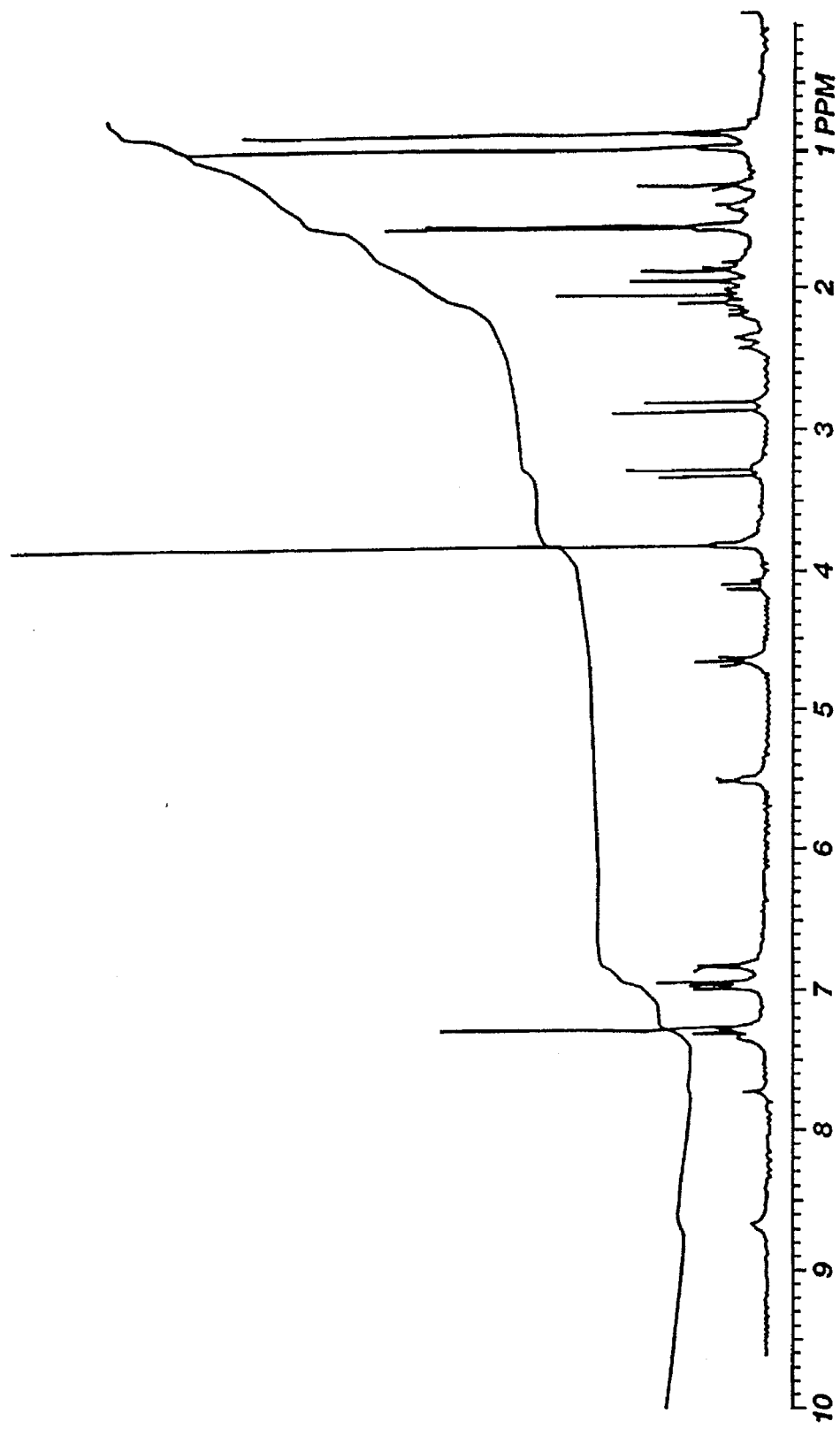
FIG. 2 is a plot of a 200 MHz $^1$H (CDCl$_3$) of camphorsulfonamide obtained from reaction of (R)-3-methoxy-α-methylbenzylamine with (+)-10-camphorsulfonyl chloride.

A preferred method of making (R)-N-[1-(3-methoxyphenyl)-ethyl]-3-(2-chlorobenzene)propanamine involves reducing N-(R)-α-methyl-3-methoxybenzyl)-3-(2-chlorobenzene)-propanamide with an appropriate reducing agent. When the compound to be reduced is an amide, the compound's carbonyl group is preferably reduced by reacting the compound with a borane-tetrahydrofuran complex. When the compound to be reduced is an imine, the compound's iminyl group is preferably reduced by reacting the compound with ethanolic sodium borohydride.

The compound to be reduced is preferably produced by the reaction of (R)-3-methoxy-α-methylbenzylamine with either β-2-chlorophenylpropionic acid or 2-(2-chloro)-phenyl-1-ethanenitrile.

Diisobutylaluminum hydride is readily commercially available from Aldrich Chemical Co. of Milwaukee, Wis.

The nitrile and amine (or chiral amine) used in the DIBAL-H embodiment of the process will generally be chosen for their respective constituent R and $R_x$ groups. The amine is preferably a primary amine. Preferably the $R_x$ groups will be selected from the group consisting of substituted or unsubstituted phenyl, lower (C1 to C4) alkyl, furanyl, pyrrolyl, and thiophenyl. Alternatively, the $R_x$ groups can be incorporated into an aromatic ring.

When the amine used in the process is (R)-3-methoxy-α-methylbenzylamine, various methods can be used to obtain it. For instance, Japanese patent application B8 41,847, 1983, describes the preparation of optically-active 3-methoxy-α-methylbenzylamine by treating the racemic form of the compound with (L)- or (D)-malic acid. Refluxing of 45.3 g of the racemic form with (L)-malic acid in 300 ml 10% ethanol/water provided 26.5 g of the diastereomer, which upon decomposition with 30% aqueous NaOH in water is described as giving 13 g of the (L) isomer. Alternatively, and as more thoroughly described herein, a method for resolving the enantiomers of 3-methoxy-α-methylbenzylamine includes refluxing the compound in an appropriate solvent with mandelic acid. It has been determined that the use of mandelic acid is advantageous over other procedures, such as refluxing in an appropriate solvent with malic acid, since it provides significantly better yields. This procedure is useful for the economical production of large quantities (kilogram and larger) of the (R) enantiomer of 3-methoxy-α-methylbenzylamine. In preferred embodiments, the method involves mixing the mandelic acid with isopropanol prior to refluxing the 3-methoxy-α-methylbenzylamine. Other solvents include ethanol and methanol.

In the formulae described herein, R is a substituted or unsubstituted alkyl, aryl, aralkyl, or is a heterocycle. R is preferably aralkyl ("Ar").

As used herein, alkyl is preferably a saturated or unsaturated, branched or unbranched hydrocarbon having one to twenty carbon atoms, e.g., methyl, ethyl, isopentyl, cycloalkyl, and allyl.

Alkoxy groups will typically have one to four carbon atoms and include groups such as methoxy and ethoxy.

Aryl, as used herein, is an aromatic hydrocarbon group, preferably having six to ten carbon atoms, such as phenyl or naphthyl or heteroaromatic such as indole and quinoline.

Aralkyl, as used herein, is a substituted or unsubstituted arene group (having both aliphatic and aromatic portions), preferably having seven to thirteen carbon atoms, such as benzyl, ethylbenzyl, n-propylbenzyl, or isobutylbenzyl.

A "substitution" with regard to the various R and Ar moieties generally relates to substituting a group such as hydroxy, alkoxy, halogen, nitro, or lower alkyl onto an aromatic ring for a hydrogen that would normally be present. Substitutions can also be made on an alkyl or alkoxy chain.

Halogen, as used herein, generally refers to fluorine, chlorine, bromine or iodine.

In the DIBAL-H embodiment of the synthesis, the nitrile, amine, and diisobutylaluminum hydride are preferably utilized in equimolar or approximately equimolar proportions (±10%). They are reacted with one another, as more completely described herein, in a preferably organic solvent such as dichloromethane or toluene. Benzene, heptane, or tetrahydrofuran (THF) may also work.

The resulting imines are generally reduced to the corresponding amines. Reducing agents for use with the process are those which will reduce the imine to an amine, but will not otherwise alter the chemical structure of the compound (e.g. ethanolic sodium cyanoborohydride or ethanolic sodium borohydride).

While not intending to be bound by any one theory relating to the DIBAL-H aspect of the invention, the following may help explain the excellent results obtained from the invention: A nitrile of the formula: R-CN, (I) is reacted with:

diisobutylaluminum hydride (DIBAL-H), (II) and is believed to form an intermediate imine-aluminum complex:

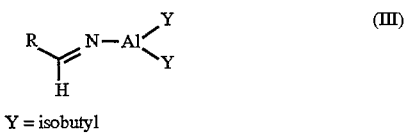

Y = isobutyl

This complex is reacted with a chiral amine of the formula:

to yield an aminal complex

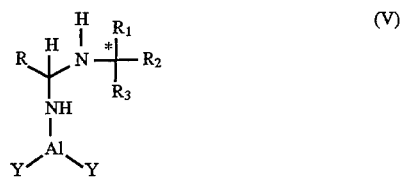

Elimination then affords the chiral imine:

If desired, this imine (V) can be reduced (e.g. by the addition of ethanolic sodium borohydride) to yield the optically pure amine:

The invention is further described by reference to the following illustrative EXAMPLES.

EXAMPLES

Example I

A. Synthesis of Racemic 3-methoxy-α-methylbenzylamine

An efficient synthesis of the title compound was developed from 3-methoxyacetophenone by a Leuckart reaction ((1) ammonium formate, reflux; (2) HCl hydrolysis). This procedure may be easily adapted to a very large scale synthesis.

1. N-[((3-Methoxyphenyl)methyl)-α-methyl]formamide

A mixture of 281 g (1.87 moles) of 3-methoxyacetophenone and 352 g (5.558 moles) of ammonium formate was stirred at 180° C. After 24 hours, TLC analysis (1:1 Hex/EtOAc) indicated that the reaction was complete. The solution was poured into water and extracted with methylene chloride. The organic layer was washed once with H$_2$O and dried with MgSO$_4$. The solution was concentrated to afford 292 g (87%) of a dark oil.

2. 3-methoxy-α-methylbenzylamine

A solution of 287 g (1.60 moles) of N-[((3-Methoxyphenyl)methyl)-α-methyl]formamide and 1400 mL of concentrated HCl was stirred at reflux. After 1.5 hours, TLC analysis (85:10:5 EtOAc/MeOH/isopropylamine) indicated the reaction was complete. The solution was concentrated to dryness and the resulting green residue was recrystallized from acetonitrile to afford a white solid. The solid was dissolved in water and the pH was raised to 12 with 50% NaOH. The product was extracted with ethyl ether. The organic layer was washed with saturated NaCl solution and dried with K$_2$CO$_3$. The solution was concentrated to afford 188.2 g (78%) of a dark oil. Distillation of 174 g of the dark oil at 760 mm Hg afforded 140 g of a clear liquid, bp 180° C.

3. Analytical Method

To determine enantiomeric purity, an analytical method was required. Because the optical rotation of the pure (R) enantiomer was determined to be only +3.8° (C=1 in 2N HCl), it was determined that optical rotation measurements would be insufficient for measuring enantiomeric excess. An NMR derivatization analysis was developed. In this procedure a sample of 3-methoxy-α-methylbenzylamine was reacted with (+)-10-camphorsulfonyl chloride in pyridine. The resulting diastereomeric camphorsulfonamides were then analyzed by proton NMR. Alternatively, an HPLC method may be adapted for use with the invention.

The NMR spectrum of the diastereomeric camphorsulfonamides obtained from racemic 3-methoxy-α-methylbenzylamine is shown in FIG. 1. When compared with the NMR spectrum of diastereomerically-pure (R)-1-(+)-camphorsulfonamide, it is clear that a number of signals are diagnostic for each enantiomer; including the sulfonamide NH signals (δ5.55 or 6.25 ppm), the camphor CH$_3$ groups (δ0.48, 0.80, 0.88 and 1.0 ppm) and the OCH$_3$ signals (δ3.78 and 3.82 ppm).

This NMR analysis is useful in terms of resolution method development. Any synthetic batches, however, may be analyzed by HPLC for the precise determinations required.

B. Resolution

The procedure of JP 58 41,847 for the resolution of (±) 3-methoxy-α-methylbenzylamine with (L)- malic acid in ethanol water was repeated using seeds generated as subsequently described. Crystallization is extremely slow and mass recovery is low. This salt was not further pursued because of the success obtained with mandelic acid, as hereinafter discussed.

Prior to experiments with malic and mandelic acids, significant efforts were first directed to the use of tartaric acid as a resolving agent. The pure (R) enantiomer of 3-methoxy-α-methylbenzylamine readily crystallized with natural tartaric acid from methanol. Unfortunately, even at high dilution, solutions of racemic 3-methoxy-α-methylbenzylamine yielded crystals too readily. Even when seeded with diastereomerically-pure seeds, the solutions would "set up", trapping large quantities of solvent in a thick lattice. For example, when 20 g of (±) 3-methoxy-α-methylbenzylamine was combined with 20 g of (+)-tartaric acid in 700 mL of hot ethanol, the solution set up as it slowly cooled to room temperature. It became clear, based upon the high mass recovery of the resultant free base and its low or nonexistent optical rotation values, that tartaric acid was not useful.

Figure 3:
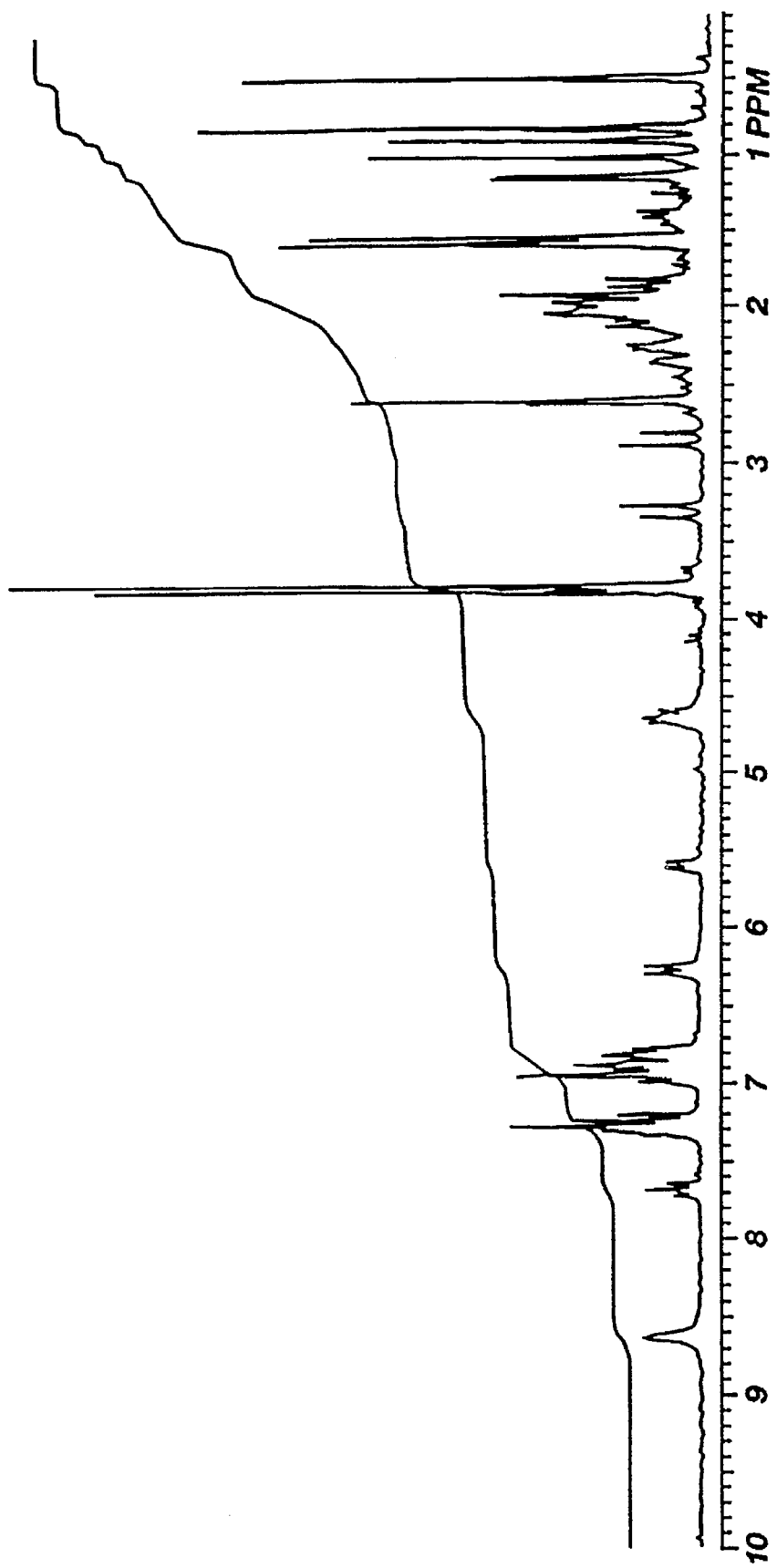
FIG. 3 is a plot of a 200 MHz $^1$H NMR (CDCl$_3$) of camphorsulfonamides obtained from reaction of 3-methoxy-α-methylbenzylamine with (+)-camphorsulfonyl chloride. The 3-methoxy-α-methylbenzylamine was previously isolated as the free base after two recrystallizations with (−)-dibenzoyl tartaric acid.

Attention was next focused on (−)-dibenzoyl tartaric acid ((−)-DET). On mixing racemic 3-methoxy-α-methylbenzylamine with one equivalent of (−)-DBT in methanol, a granular precipitate immediately developed. This was in contrast to the thick lattice that resulted from tartaric acid. Recrystallization of the (−)-DBT salt obtained from (±) 3-methoxy-α-methylbenzylamine yielded slow plate formation. Two factors were disappointing about (−)-DBT, however. First, mass recovery was not good. Second, after two recrystallizations from methanol, it was apparent by NMR analysis of the derived (+)-camphorsulfonamide (FIG. 3) and optical rotation $[\alpha]_D=-1.0°$ (C=1.0 in 2N HCl) that 3-methoxy-α-methylbenzylamine was enantiomerically enhanced in the undesired direction.

1.5 g of (R) 3-methoxy-α-methylbenzylamine was used, in part, to generate seed crystals as the salt of a number of acidic resolving agents. The following resolving agents were added (one equivalent) to a methanolic solution of (R) 3-methoxy-α-methylbenzylamine: (+)-10-camphorsulfonic acid; (−)-10-camphorsulfonic acid; (L)-malic acid; (D)-malic acid; (−)-mandelic acid; (+)-mandelic acid; (+)-dibenzoyl tartaric acid; (R)-(−)-1,1'-binaphthyl-2,2-diylhydrogen phosphate; and, (S)-(+)-1,1'-binaphthyl-2,2-diylhydrogen phosphate. Only the solution containing (+)-DBT readily crystallized at this concentration in methanol. After slight evaporation, crystals were also obtained of the (−)-mandelic acid salt. The (+)-mandelate did not yield crystals until evaporation of the methanol was nearly completed.

Figure 4:
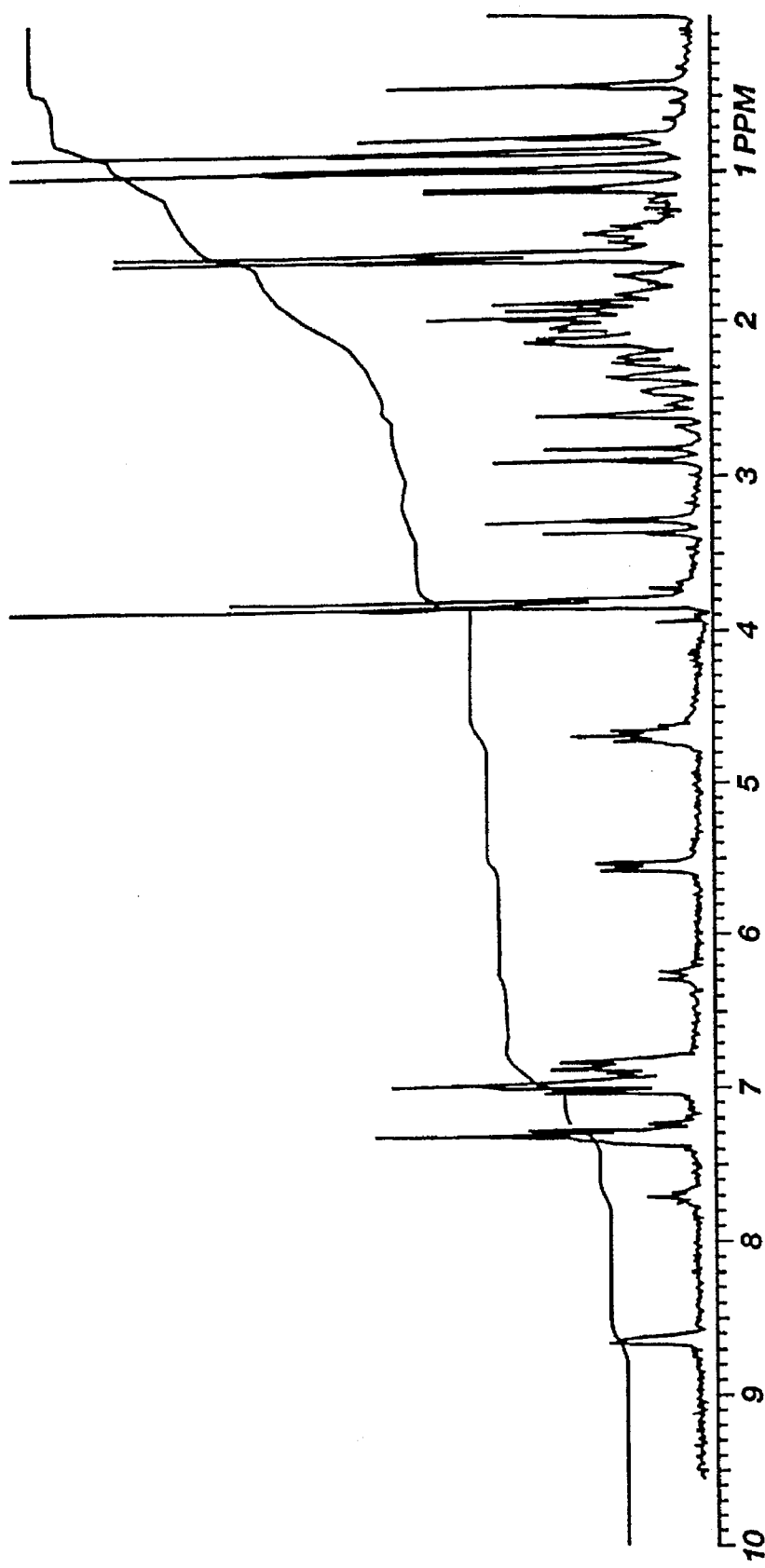
FIG. 4 is a plot of a 200 MHz $^1$H NMR (CDCl$_3$) of camphorsulfonamides obtained from reaction of 3-methoxy-α-methylbenzylamine with (+)-10 camphorsulfonyl chloride. The 3-methoxy-α-methylbenzylamine was previously isolated as the free base after two recrystallizations with (+)-dibenzoyl tartaric acid.

When (+)-DBT was used as the resolving agent and the solution seeded with diastereomerically-pure crystals, the results were very promising. FIG. 4 shows the NMR spectrum obtained from the camphorsulfonamide after two recrystallizations. This material is a mixture of the two enantiomers of 1, greater than a 3:1 ratio in the desired sense.

Figure 5:
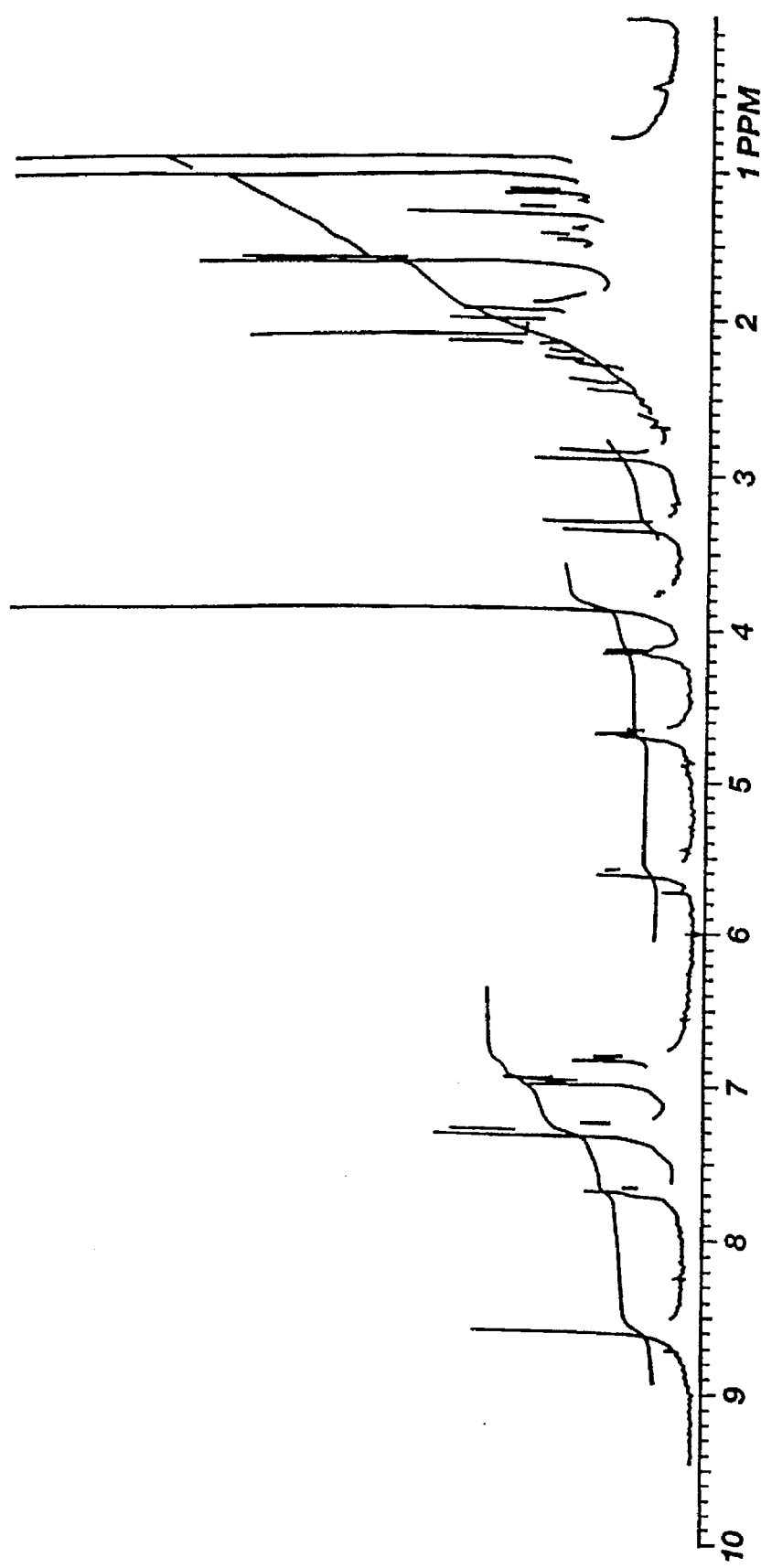
FIG. 5 is a plot of a 200 MHz $^1$H NMR (CDCl$_3$) of camphorsulfonamides obtained from reaction of 3-methoxybenzylamine with (+)-camphorsulfonyl chloride. The 3-methoxy-α-methylbenzylamine was previously isolated as the free base after one recrystallization with (R)-(−)-mandelic acid.

Although the results with (+)-DBT as a resolving agent were promising, even better was the use of (−)-mandelic acid. One crystallization (on a 10 game scale) with hot isopropanol with seeding afforded diastereomeric salt containing 3-methoxy-α-methylbenzylamine that was nearly enantiomerically pure (see FIG. 5). Furthermore, mass recovery was good on this initial attempt, yielding 70% of theory. A second batch of (±) 3-methoxy-α-methylbenzylamine was prepared to repeat this resolution on a slightly larger scale.

C. (R)-3-methoxy-α-methylbenzylamine

A solution of 14.0 g (92.0 mmol) of (R)-(−)- mandelic acid (Aldrich, 99+%), 14.0 g (92.7 mmol) of (±) 3-methoxy-α-methylbenzylamine and 500 mL of isopropanol was brought to reflux and gravity filtered while hot. The solution was then seeded at 50° C. with diastereomerically-pure seeds. After cooling to room temperature, the mixture was filtered to afford 10.9 g of a fluffy, white solid. This was recrystallized from 500 mL of isopropanol. The solids were collected then partitioned between ethyl acetate and saturated Na$_2$CO$_3$. The organics were washed with saturated NaCl, dried with Na$_2$SO$_4$, and concentrated to afford 5.8 g (83%) of a yellow oil. NMR analysis of the derived camphorsulfonamide (FIG. 6) indicated that the chemical is enantiomerically pure, to the limits of detection of NMR. This oil was distilled, b.p. 118°–120° C. at aspirator pressure, $[\alpha]_D=+3.8°$ (c+1 in 2N HCl). Preliminary results suggest that this compound may form a carbonate upon exposure to air. It is therefore recommended that the chemical be stored under an inert atmosphere.

Example II

A. Imine formation: A 100 ml round-bottomed flask equipped with magnetic stir bar, septum, and nitrogen source, was charged with 2-(2-chloro)-phenyl-1-ethanenitrile (4,996 g, 30,165 mmole, ≈4.4 ml) in dichloromethane (26 ml giving a total volume of ≈30 ml, ≈1M in nitrile) and treated @−78° C. with DIBAL-H (4.333 g, 30.467 mmol, 1.01 Eq.) at a rate of 0.5 ml/min. After the addition, the reaction was removed from the −78° C. bath and stirred at room temperature for 60 min. After this time, the reaction was cooled to −78° C. and treated with (R)-3'-methoxy-α-methylbenzylamine (4,555 g, 30,165 mmol, ≈4.4 ml) dropwise over 2 min. The reaction was stirred in the −78° C. bath and allowed to warm slowly to room temperature, where it remained overnight (20 hour reaction time after the addition of amine).

B. Reduction to form amine: The reaction was then treated directly with sodium borohydride (1.2 g, 31.72 mmol) followed by the slow addition of ethanol (10 ml) at a rate of 2 ml per hour. After the addition of ethanol, the reaction was quenched with 10% HCl (100 ml).

C. Separation and analysis: The acidic solution was basified (pH>12) by the addition of 10N NaOH and extracted with diethyl ether (300 ml). The ether layer was separated, dried over anhydrous $MgSO_4$, and concentrated to an oil. GC-EI-MS analysis of this material showed a single component, the product, NPS R-568. TLC analysis (silica) with 3% (v/v) methanol in dichloromethane showed two UV active components at Rƒ 0.45 (product) and Rƒ 0.29. Spraying with ninhydrin (1° amines) and heating showed four additional minor components at Rƒ 0.99, 0.51, 0.33, and 0.0. The component at Rƒ 0.99 gave a true ninhydrin positive reaction. The components at Rƒ 0.99, 0.45, 0.33, and 0.29 gave a positive response to Dragendorff's (2° and 3° amines) reagent. One additional minor component was observed at Rƒ 0.95 with iodoplatinate spray reagent (amines). The reaction mixture was chromatographed through silica (22×10 cm i.d.) using a gradient of hexane to dichloromethane (containing 1% (v/v) isopropylamine) to 3% (v/v) methanol in dichloromethane (containing 1% (v/v) isopropylamine) to afford 6.990 g (76%) of the compound (E)-α-[1-(3-methoxyphenyl)ethyl]-3-(2-chlorobenzene)propanamine (also known as N-[3-(2-chlorophenyl)propyl]-R-α-methyl-3-methoxybenzylamine or NPS E-568).

Example III

A. Diethyl o-Chlorobenzylmalonate

To a 50 liter flask, under argon atmosphere, was added ethyl alcohol (200 proof, 14.4 kg, 18,244 mL) and sodium metal (611.0 g, 26.58 mol). When the sodium metal has dissolved, the resulting solution was cooled to 15°±3° C. To this solution was added diethyl malonate (5.46 kg, 34.09 mol) as rapidly as possible while maintaining the internal temperature at 15°±3° C. The reaction was allowed to stir for 30 minutes and was then cooled to 5°±5° C. To this solution was added 2-chlorobenzyl chloride (4.26 kg, 26.45 mol) at such a rate that the internal reaction temperature was maintained at 5°±5° C. The reaction was allowed to stir at 5°±5° C. for two hours and then heated at reflux for one hour. The reaction was then allowed to cool overnight with stirring.

The ethyl alcohol was removed in vacuo and ethyl acetate (11L) was added to the residue. The organic phase was extracted with water (11L), dried ($Na_2SO_4$, 4 kg) and concentrated. The product was purified by vacuum distillation to give diethyl o-chlorobenzylmalonate (6102 g, 81.2%, bp 161°–162° C.@0.3–0.4 mmHg) as a clear colorless liquid.

B. β-2-Chlorophenylpropionic Acid

To a 50 liter flask was added diethyl o-chlorobenzylmalonate (6067 g, 21.31 mol), glacial acetic acid (1090 mL), and concentrated hydrochloric acid (16,000 mL). The reaction was then heated at reflux for 21 hours and 13 minutes. Additional concentrated hydrochloric acid (1840 mL, 5520 mL total) was added at 3.5, 13.5, and 17 hours into the reflux. The reaction was cooled to 0°±2° C. and the resulting solid was collected by suction filtration and washed with water (4L). The solid was suspended in water (8L) and the slurry was stirred for five minutes. The solid was collected by suction filtration and washed with water (20L). The filtrate was pH 2 and tested positive for chlorine. The solid was then washed seven times in the following manner; the solid was suspended in water (8L) and stirred for approximately ten minutes. The solid was collected by suction filtration and washed with water (4L). The filtrate was tested for chloride ion and the pH was recorded. The final filtrate was pH 4.5–5 and tested negative to the presence of chloride ion. A total of 100 liters of water was used to wash the solid. The solid was dried under vacuum at 35°±3° C. for 70 hours to give crude β-2-chlorophenylpropionic acid (3653 g, 93.4%) as a white solid.

Crude β-2-chlorophenylpropionic acid (3644.7 g, 19.74 mol) was dissolved in toluene (10.2 L) at 60°±10° C. The solution was cooled to 50°±10° C. and petroleum ether was added (35°–60° C., 23L). The solution was heated until all of the solid dissolved. The solution was allowed to cool to room temperature and was then cooled to 0°±2° C. The resulting slurry was stirred at 0°±2° C. for two hours. The solid was collected by suction filtration and washed with petroleum ether (35°–60° C., 5 L). The solid was dried under vacuum at 25°±2° C. for 25 hours to give β-2-chlorophenylpropionic acid (3348 g, 91.9%) as a white solid.

C. N-((R)-α-Methyl-3-methoxybenzyl)-3-(2-chlorobenzene) propanamide

To a solution of toluene (6000 mL) under argon atmosphere was added β-2-chlorophenylpropionic acid (2930.7 g, 15.87 mol) and (R)-3-methoxy-α-methylbenzylamine (2045.4 g, 13.53 mol). The reaction was heated at reflux for 55 hours with azeotropic removal of water using a Dean-Stark trap. The reaction was allowed to cool and was then diluted with ethyl acetate (21.3 kg, 23.6L). The organic solution was extracted with 10% hydrochloric acid (3×13.5 kg), 4% sodium hydroxide (3×13.5 kg) and brine (3×14L). The organic phase was dried ($Na_2SO_4$, 5 kg) and concentrated in vacuo. The resulting solid was dried under vacuum at 35°±2° C. for 22 hours to give N-((R)-α-methyl-3-methoxybenzyl)-3-(2-chlorobenzene)propanamide (4023.3, 93.8%) as a solid.

D. Reduction to form (R)-N-(3-methoxy-α-phenylethyl)-3-(2'-chlorophenyl)-1-propylamine HCl

To a 0°±5° C. solution of borane-tetrahydrofuran complex (1.0M, 17.94 kg, 19,978 mL, 19.98 mol) in a 50 liter flask under argon atmosphere was added a solution of N-((R)-α-methyl-3-methoxybenzyl)-3-(2-chlorobenzene) propanamide (3799.8 g, 11.96 mol) dissolved in tetrahydrofuran (4700 mL). The addition took place over a period of one hour and nineteen minutes. The temperature of the reaction solution rose from 1° C. to 14° C. during the course of the addition. With vigorous stirring, the reaction was heated to 68°±3° C. for two hours. The reaction was cooled to 3°±5° C. and a solution of 6M hydrochloric acid (13,200 mL) was slowly added to the reaction. Tetrahydrofuran (18,100 mL) was removed from the reaction flask by distillation at ambient pressure. Water (10L) was added to the reaction flask and the solution was cooled to 0°±5° C. The resulting solid was collected by suction filtration. The solid was washed with 5°±5° C. water (3×4000 mL) and dried under vacuum at 50°±5° C. for 98 hours to give crude (R)-N-(3-methoxy-α-phenylethyl)- 3-(2'-chlorophenyl)-1-propylamine HCl (4630.2 g, 114.7%) as a white solid.

To a 22 liter flask was added crude (R)-N-(3-methoxy-α-phenylethyl)-3-(2'-chlorophenyl)-1-propylamine HCl (4626 g, 13.59 mol), ethyl alcohol (200 proof, 4280 mL), and water (4 L). The solution was heated at reflux until all of the solid had dissolved. The hot solution was gravity filtered into a 50 liter flask. The 22 liter flask was rinsed with a solution of ethyl alcohol:water (1:1, 1000 mL) and filtered into the 50 liter flask. Water (31L) was added to the filtered solution and the solution was heated until all of the solid dissolved. [Solid dissolved at 95° C.] The solution was allowed to cool to room temperature and then was cooled to 0°±2° C. The resulting slurry was stirred at 0°±2° C. for one hour. The solid was collected by suction filtration, washed with 5°±5° C. water (4L) and dried under vacuum at 50°±5° C. for 122 hours to give (R)-N-(3-methoxy-α-phenylethyl)-3-(2'-chlorophenyl)-1-propylamine HCl (3711.7 g, 92%) as a white solid.

Example IV

In a manner similar to the one described in Example II, except substituting the hereinafter-identified appropriate nitrile for 2-(2-chloro)-phenyl-1-ethanenitrile and the hereinafter-identified appropriate amine for (R)-3'-methoxy-α-methylbenzylamine, the following were prepared:

A. tribenzylamine; (nitrile: benzonitrile; amine: dibenzylamine) GC-MS($R_f$=10.06 min), m/z (rel. int.) 287 ($M^+$, 16), 210 (13), 196 (12), 91 (100).

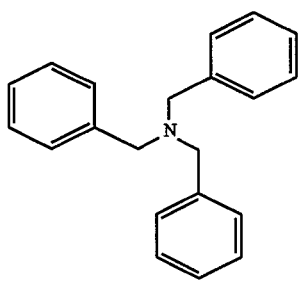

B. N-isopropylbenzylamine; (nitrile: benzonitrile; amine: isopropylamine) GC-MS($R_f$=3.15 min), m/z (rel. int.) 149($M^+$, 3), 134(37), 91(100).

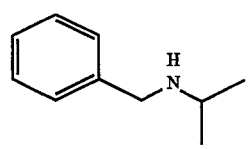

C. N-tert-butylbenzylamine; (nitrile: benzonitrile; amine: tert.-butylamine) GC-MS($R_f$=3.47 min.), m/z (rel. int.) 163($M^+$, 2), 148(93), 91(100), 77(12).

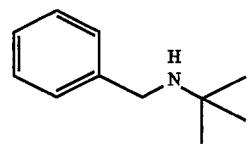

D. N-isopropyl-3-phenyl-1-propylamine; (nitrile: 3-phenylpropionitrile; amine: isopropylamine) GC-MS ($R_f$=4.69 min), m/z(rel. int.) 177($M^+$, 21), 162(74), 117 (11), 103(9), 91(100), 72(51), 58(36).

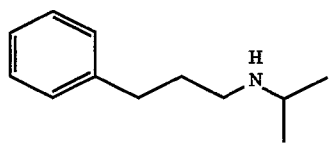

E. N,N'-dibenzyl-3-phenyl-1-propylamine; (nitrile: 3-phenylpropionitrile; amine: dibenzylamine) GC-MS ($R_f$=11.05 min), m/z(rel. int.) 315($M^+$, 9), 224(15), 210 (100), 181(6), 118(5), 105(5), 91(98).

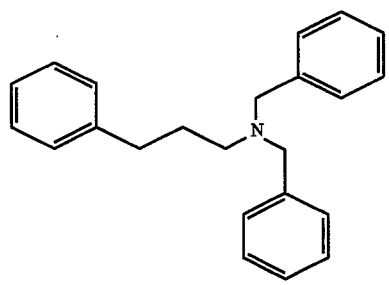

F. N-phenyl-3-phenyl-1-propylamine; (nitrile: 3-phenylpropionitrile; amine: aniline) GC-MS($R_f$=8.38 min), m/z (rel. int.) 311 ($M^+$, 44), 118(7), 106(100), 91 (24), 77 (29).

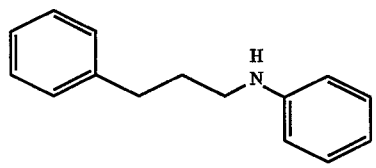

G. N-(4-methoxyphenyl)-3-phenyl-1-propylamine; (nitrile: 3-phenylpropanonitrile; amine: p-methoxyaniline) GC-MS($R_f$=9.70 min), m/z(rel. int.) 241($M^+$, 75),226(7), 136(100), 91(35), 77(11).

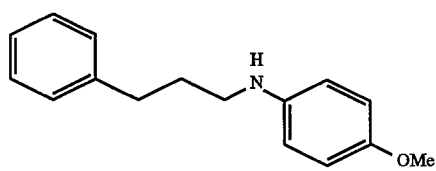

H. N-(4-bromophenyl)-3-phenyl-1-propylamine; (nitrile: 3-phenylpropionitrile; amine: p-bromoaniline) GC-MS ($R_f$=10.26 min), m/z (rel. int.) 291/289 ($M^+$, 56), 186/184 (100), 173/171 (14), 157/155 (8), 105 (25), 91 (47), 77 (14).

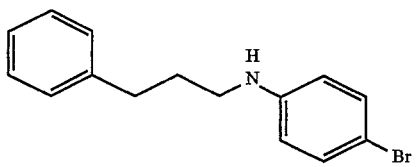

I. (R)-N-[3-(3-methylphenyl)-prop-2-en-1-yl]-1-α-naphthylethyl amine; (nitrile: 3-(3-methyl)phenyl proprionitrile-2-ene amine: (R)-(+)-1-(1-naphthyl) ethylamine. GC-MS(R$_t$=11.73 min), m/z(rel. int.) 301(M$^+$, 10), 286 (9), 155 (100), 131 (67), 115 (76), (44), 77 (22).

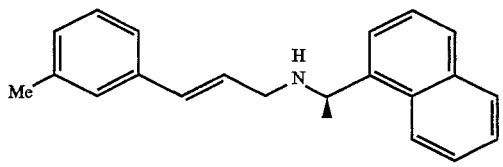

References herein to specific Examples or embodiments should not be interpreted as limitations to the invention's scope, which is determined by the claims.

What is claimed is:

1. A method of making (R)-N-[1-(3-methoxyphenyl)-ethyl]-3-(2-chlorobenzene)propanamine comprising: reducing a compound of the formula:

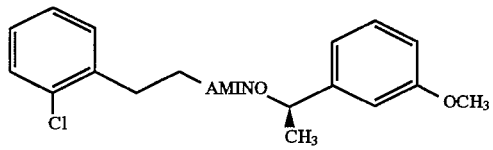

wherein AMINO is either:

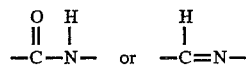

to form

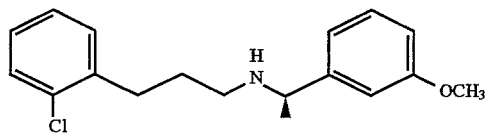

2. The method of claim 1 wherein AMINO is

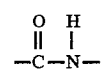

and the compound's carbonyl group is reduced by reacting the compound with a borane-tetrahydrofuran complex.

3. The method of claim 1 wherein AMINO is

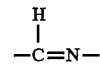

and the compound's iminyl group is either catalytically reduced or reduced by reacting the compound with ethanolic sodium cyanoborohydride or ethanolic sodium borohydride.

4. The method of claim.1 wherein the compound is produced by the reaction of R-3-methoxy-α-methylbenzylamine with either β-2-chlorophenylpropionic acid or 2-(2-chloro)-phenyl-1-ethanenitrile.

5. The method of claim 4 wherein said R-3-methoxy-α-methylbenzylamine is produced by resolving enantiomers of 3-methoxy-α-methylbenzylamine by a method comprising refluxing said 3-methoxy-α-methylbenzylamine in an appropriate solvent with R-(−)-mandelic acid.

* * * * *

UNITED STATES PATENT AND TRADEMARK OFFICE
CERTIFICATE OF CORRECTION

PATENT NO. : 5,648,540
DATED : July 15, 1997
INVENTOR(S) : VanWagenen et al.

It is certified that error appears in the above-identified patent and that said Letters Patent is hereby corrected as shown below:

On the Title Page under "Foreign Patent Documents" - 3 Japanese patents have been omitted: (1) 0069008 - 4/85; (2) 4018058 - 1/92; (3) 6001757 - 1/94

In Column 3, line 15, change "B8" to --58--
In Column 5, line 45, change "($\pm$)" to --($\pm$ --
In Column 5, line 47, after "ethanol" insert -- - -- (hyphen)
In Column 7, line 05, change "(4,996g, 30, 165" to --(4.996g, 30.165--
In Column 7, line 12, change "(4,555g, 30, 165" to --(4.555g, 30.165--
In Column 7, line 41, change "(E)-$\alpha$-" to --(R)-N- --
In Column 7, line 44, change "NPS E-568)" to --NPS R-568)--
In Column 11, line 14, before "(44)," insert --91--

Signed and Sealed this

Tenth Day of November 1998

Attest:

BRUCE LEHMAN

*Attesting Officer*     *Commissioner of Patents and Trademarks*